United States Patent [19]

Hirai

[11] Patent Number: 5,411,029
[45] Date of Patent: May 2, 1995

[54] BIOLOGICAL SIGNAL MEASURING DEVICE

[75] Inventor: Masaaki Hirai, Tokyo, Japan

[73] Assignee: Nihon Kohden Corporation, Tokyo, Japan

[21] Appl. No.: 212,923

[22] Filed: Mar. 15, 1994

[30] Foreign Application Priority Data

Mar. 15, 1993 [JP] Japan .................. 5-053784

[51] Int. Cl.$^6$ ................................ A61B 5/04
[52] U.S. Cl. ..................... 128/696; 128/731
[58] Field of Search ............... 128/696, 703, 704, 902, 128/731, 733, 681

[56] References Cited

U.S. PATENT DOCUMENTS 4,546,776 10/1985 Bellin et al. .................. 128/704
4,796,638 1/1989 Sasaki ........................... 128/704

Primary Examiner—William E. Kamm
Assistant Examiner—Scott M. Getzow
Attorney, Agent, or Firm—Sughrue, Mion, Zinn, Macpeak & Seas

[57] ABSTRACT

An object of this invention is to provide a biological signal measuring device which is able to reproduce a biological signal waveform with high fidelity which is detected from an object under examination. The biological signal measuring device comprises: an amplifier and a filter forming a waveform leading section which has a filter characteristic represented by a predetermined transfer function and filters a biological signal waveform detected from an object under examination; a waveform cutting section for extracting a desired part of the biological signal waveform outputted by the waveform leading section; and a reverse correction circuit for subjecting the part thus extracted to reverse correction with a transfer function which is opposite to that of the waveform leading section.

3 Claims, 3 Drawing Sheets

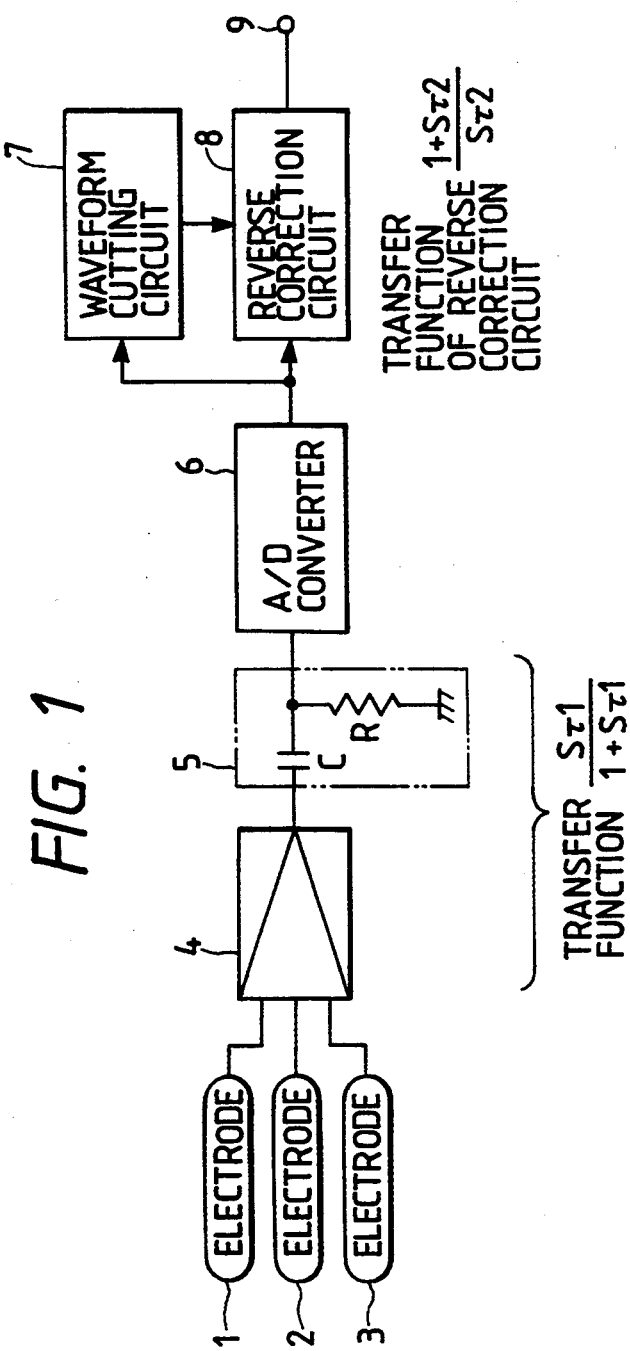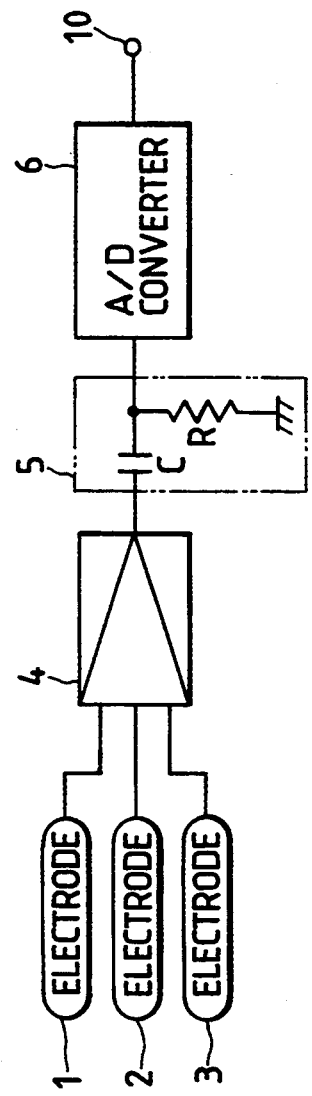

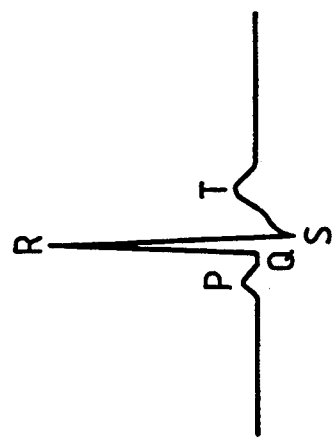
FIG. 2
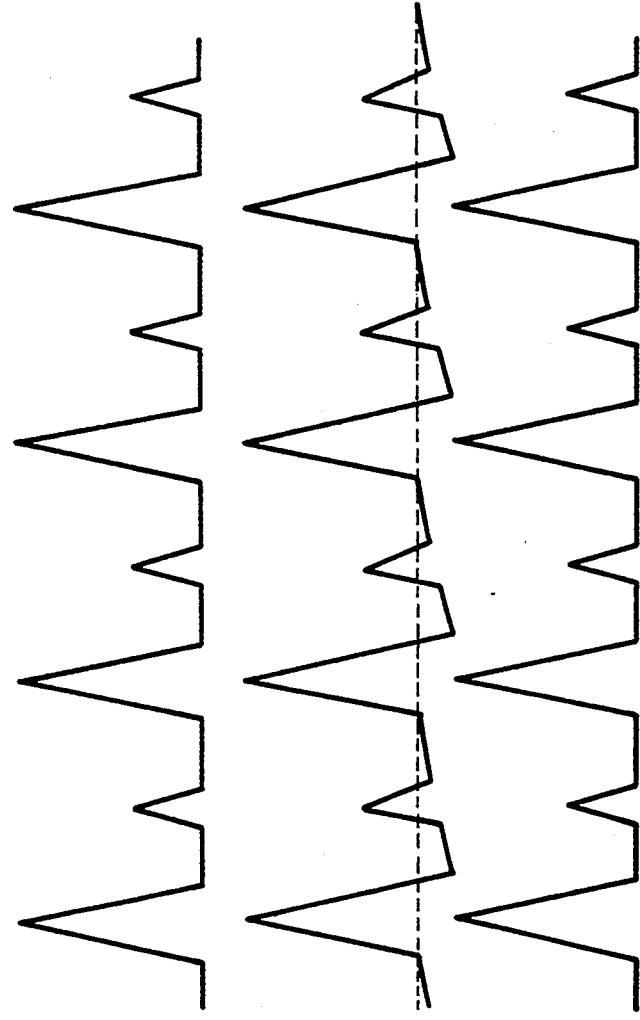
FIG. 3(a)
FIG. 3(b)
FIG. 3(c)

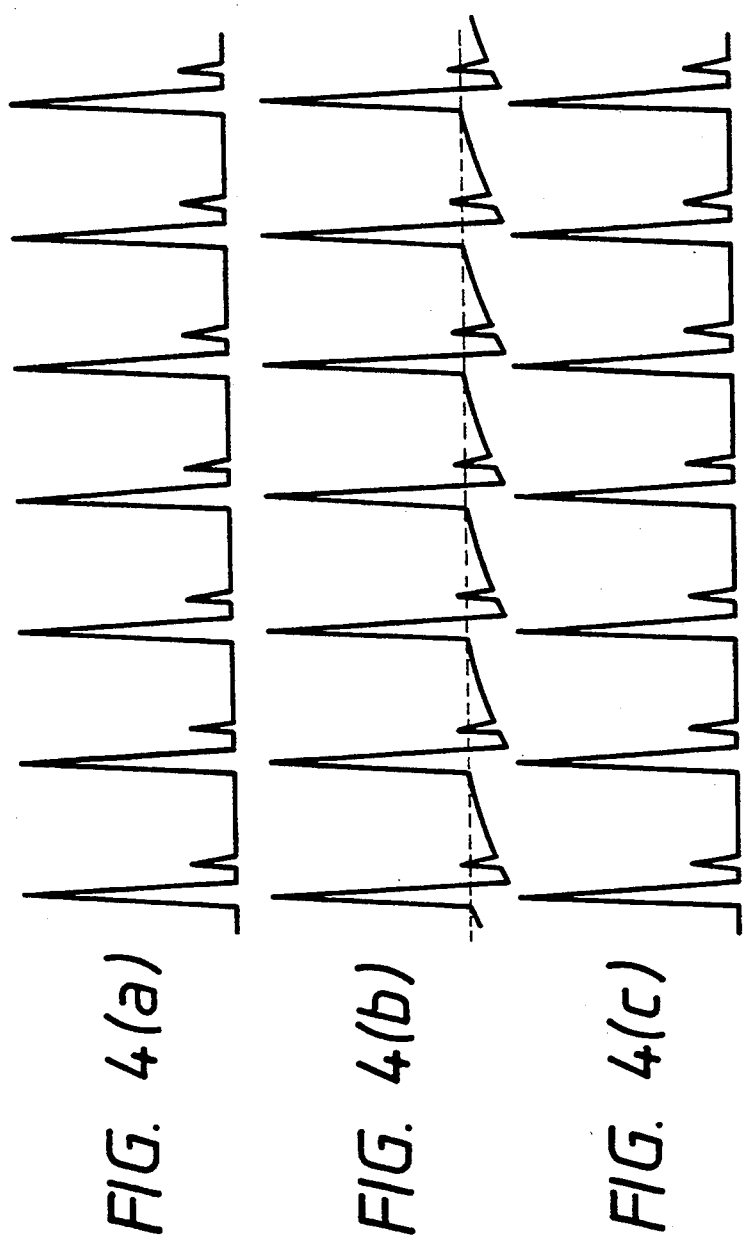

BIOLOGICAL SIGNAL MEASURING DEVICE

BACKGROUND OF THE INVENTION

1. Field of the invention

This invention relates to a biological signal measuring device which reproduces a biological signal waveform such as an electrocardiogram with high fidelity which is detected from an object under examination.

2. Related Art

One example of a conventional biological signal measuring device provided for an electrocardiogram is designed as shown in FIG. 5. In the device, signals detected through electrodes 1, 2 and 3 are amplified by an amplifier 4 and applied to a filter 5. The output signals of the filter 5, namely, electrocardiogram waveforms are applied to an A/D (analog-to-digital) converter 6, where they are converted into digital signals, which are applied to an output terminal 10. The waveform data provided at the output terminal 10 are processed, for instance, by a waveform displaying section, so that they are displayed on the screen of a CRT (cathode ray tube).

In order to obtain stable electrocardiograms, the filter 5 of the biological signal measuring device is made small in time constant.

As was described above, in the conventional biological signal measuring device, the biological signals are applied to the filter 5 short in time constant to obtain stable waveforms. Hence, when a triangular pulse wave as shown in FIG. 3 (a) or in FIG. 4 (a) is applied to the filter 5, the output waveform of the filter 5 is distorted as shown in FIG. 3 (b) or in FIG. 4 (b).

Therefore, when it is required to observe the ST segment of an electrocardiogram for the diagnosis of the ischemia due to cardiac infarction or angina pectoris, the following difficulty is involved: the ST segment are distorted, and accordingly it is difficult to analyze the waveforms.

Furthermore, for instance in the case of measuring an cardiac output, a preparatory operation must be carried out; that is, before the measurement is started, a zero point adjustment must be carried out to prevent the distortion of the waveform. The preparatory operation to be carried out before the measurement is rather trouble.

SUMMARY OF THE INVENTION

Accordingly, an object of this invention is to eliminate the above-described difficulties accompanying a conventional biological signal measuring device. More specifically, an object of the invention is to provide a biological signal measuring device which is able to reproduce biological signal waveforms with high fidelity which are detected from an object under examination.

According to an aspect of the present invention, a biological signal measuring device comprises: a waveform leading circuit, having a predetermined transfer function, for filtering a biological signal waveform detected from an object under examination; and reverse correction circuit for correcting the biological signal waveform outputted by the waveform leading circuit with a transfer function opposite in characteristic to the transfer function of the waveform leading circuit, to reproduce the original waveform of the biological signal waveform.

According to another aspect of the present invention, a biological signal measuring device comprises a waveform leading circuit, having a predetermined transfer function, for filtering a biological signal waveform detected from an object under examination; a waveform cutting circuit for extracting a desired part of the biological signal waveform outputted by the waveform leading circuit; and a reverse correction circuit for correcting the part of the biological signal waveform extracted by the waveform cutting circuit with a transfer function opposite in characteristic to the transfer function of the waveform leading circuit, to reproduce the original waveform of the biological signal waveform.

The device of the invention operates as follows: A desired part of the biological signal waveform outputted by the waveform leading circuit having a filter characteristic represented by a predetermined transfer function is extracted, and the part thus extracted is subjected to reverse conversion by a reverse collection circuit whose transfer function is opposite in characteristic to that of the waveform leading circuit. Hence, the original waveform of the biological signal waveform can be reproduced with high fidelity.

BRIEF DESCRIPTION OF THE DRAWINGS

FIG. 1 is a block diagram showing one example of a biological signal measuring device according to this invention.

FIG. 2 is a waveform diagram showing an electrocardiogram which is one of the items to be measured with the biological signal measuring device according to the invention.

FIG. 3 (a) is a waveform diagram showing an original waveform applied to the device of the present invention;

FIG. 3 (b) is a waveform diagram showing the output signal of a conventional biological signal measuring device;

FIG. 3 (c) is also a waveform diagram showing the output signal of the biological signal measuring device of the present invention;

FIG. 4 (a) is a waveform diagram showing another original waveform applied to the device of the present invention;

FIG. 4 (b) is a waveform diagram showing the output signal of the conventional biological signal measuring device;

FIG. 4 (c) is also a waveform diagram showing the output signal of the biological signal measuring device of the present invention;

FIG. 5 is a block diagram showing the arrangement of the conventional biological signal measuring device.

DETAILED DESCRIPTION OF THE PREFERRED EMBODIMENTS

A biological signal measuring device according to this invention will be described with reference to the accompanying drawings in detail.

FIG. 1 is a block diagram showing an example of the biological signal measuring device which is employed for electro-cardiograms. In the device, electrodes 1, 2 and 3 are coupled to parts of a human body under examination, to detect biological signal therefrom. The biological signals thus detected are applied to an amplifier 4, where they are amplified. The output signals of the amplifier 4 are applied to a filter, so that electrocardiograms are obtained. The filter is made up of a capacitor C series-connected to the signal line, and a resistor R connected between the output side of the capacitor and ground. The amplifier 4 and the filter 5 form a waveform leading section. Depending on the characteristic of the filter 5, the transfer function A of the waveform leading section is represented by the following equation:

$$A = \frac{S\tau_1}{1 + S\tau_1}$$

where, S: Laplacean; $t_1$: time constant.

The output signals of the filter 5 are applied to an A/D converter 6, where they are converted into digital signals, which are applied to a waveform cutting section 7 and a reverse correction circuit 8. The waveform cutting section 7 operates as follows: It is assumed that an electrocardiogram includes a P wave, a Q wave, an R wave, an ST segment, and it is required to observe the S and T waves. In this case, the waveform cutting section 7 operates to extract the ST segment, which are applied to the reverse correction circuit 8. In the case where no wave is extracted, the output signal of the A/D converter 6 is applied directly to the reverse correction circuit 8.

The reverse correction circuit 8 has a transfer function B which is opposite in characteristic to the transfer function A of the waveform leading section (hereinafter referred to as "a reverse transfer function B", when applicable). The reverse transfer function B is represented by the following equation:

$$B = \frac{1 + S\tau_2}{S\tau_2}$$

where, S: Laplacean and $t_2$: time constant.

In the reverse correction circuit 8 having the above-described reverse transfer function B, waveform data inputted with t1=t2 is subjected to reverse conversion. Hence, the original waveform of the biological signal waveform is reproduced with high fidelity. As a result, for instance the ST segment of an electrocardiogram can be extracted with no distortion; that is, the waveforms can be observed with high accuracy.

The biological signal waveform provided at the output terminal, which corresponds to the original waveform with high fidelity, is applied to a display signal processing section or the like, where it is displayed on a monitoring screen or recorded with a recorder.

As is apparent from the above description, with the biological signal measuring device according to the invention, the original waveform can be reproduced with high fidelity. Hence, when the original wave (triangular pulse wave) as shown in FIG. 3 (a) is applied to the device, it is reproduced accurately as shown in FIG. 3 (c). Furthermore, in the case where an original wave, which is similar to an electrocardiogram as shown in FIG. 4 (a), is applied to the device, it is reproduced with high fidelity as shown in FIG. 4 (c).

The invention has been described with reference to an electrocardiogram; however, the invention is not limited thereto or thereby. That is, the technical concept of the invention may be applied to the measurement of other biological signal waveforms, for instance, in the analysis of blood pressure waveforms, in the measurement of cardiac outputs, in the measurement of oxygen saturation, and in the measurement of brain waves.

In the biological signal measuring device, a biological signal waveform detected from an object under examination is applied to the waveform leading section, where it is subjected to filtration. Thereafter, a desired part of the biological signal waveform outputted by the waveform leading section is extracted, and the part thus extracted is corrected by the reverse correction circuit whose transfer function is opposite in characteristic to that of the waveform leading section. Hence, the original waveform of the biological signal waveform is reproduced with high fidelity.

Therefore, for instance the ST segment of an electrocardiogram which heretofore unavoidably suffers from measurement error being distorted, can be measured with high accuracy according to the invention.

Furthermore, the original waveform is reproduced with high fidelity. Therefore, in measuring cardiac outputs, it is unnecessary to perform the zero point adjustment before it is started. That is, the measurement can be achieved with ease.

In addition, the output signal of the device is free from phase distortion. Therefore, in the measurement of oxygen saturation or in the analysis of blood pressure waveforms, the waveforms can be processed with high accuracy; that is, the measurement according to the invention is much higher in accuracy than that according to the prior art.

What is claimed is:

1. A biological signal measuring device comprises:
   a waveform leading circuit, having a predetermined transfer function, for filtering a biological signal waveform detected from an object under examination; and
   a reverse correction circuit for correcting the biological signal waveform outputted by the waveform leading circuit with a transfer function opposite in characteristic to the transfer function of the waveform leading circuit, to reproduce the original waveform of the biological signal waveform.

2. A biological signal measuring device as claimed in claim 1, further comprising:
   a waveform cutting circuit for extracting a desired part of the biological signal waveform outputted by the waveform leading circuit,
   wherein the reverse correction circuit corrects the part of the biological signal waveform extracted by the waveform cutting circuit with a transfer function opposite in characteristic to the transfer function of the waveform leading circuit to reproduce the original waveform of the biological signal waveform.

3. A biological signal measuring device as claimed in claim 1, the transfer function A of waveform leading circuit is expressed by the following equation:

$$A = \frac{S\tau_1}{1 + S\tau_1}$$

where, S: Laplacean; and $_1$: a first time constant and, wherein the transfer function B of the reverse correction circuit is expressed by the following equation:

$$B = \frac{1 + S\tau_2}{S\tau_2}$$

where, S: Laplacean; and $t_2$: a second time constant.

* * * * *